United States Patent [19]

Keil et al.

[11] Patent Number: 5,009,702
[45] Date of Patent: Apr. 23, 1991

[54] CYCLOHEXENONE COMPOUNDS AND USE AS HERBICIDES OR AS PLANT GROWTH REGULATORS

[75] Inventors: Michael Keil, Freinsheim; Ulrich Schirmer, Heidelberg; Juergen Kast, Boehl-Igggelheim; Dieter Kolassa, Ludwigshafen; Bruno Wuerzer, Otterstadt; Norbert Meyer, Ladenburg; Wilhelm Rademacher; Johann Jung, both of Limburgerhof, all of Fed. Rep. of Germany; Dale R. Carlson, Durham, N.C.

[73] Assignee: BASF Aktiengesellschaft, Ludwigshafen, Fed. Rep. of Germany

[21] Appl. No.: 327,352

[22] Filed: Mar. 22, 1989

Related U.S. Application Data

[63] Continuation-in-part of Ser. No. 240,465, Sep. 2, 1988, abandoned, which is a continuation-in-part of Ser. No. 201,891, Jun. 3, 1988, abandoned.

[51] Int. Cl.⁵ .................... A01N 37/00; C07C 327/00
[52] U.S. Cl. ............................. 71/100; 558/257; 558/250; 558/252; 558/256
[58] Field of Search .............. 558/257, 250, 252, 256; 71/100

[56] References Cited

U.S. PATENT DOCUMENTS 3,849,466 11/1974 Henrick et al. ............... 558/250
4,249,937 2/1981 Iwataki et al. ................ 558/257
4,560,403 12/1985 Motojima et al. ............. 558/257
4,584,013 4/1980 Brunner ....................... 558/257
4,640,700 2/1987 Brunner ....................... 558/257

FOREIGN PATENT DOCUMENTS 1205831 7/1982 Canada ....................... 558/257
177450 4/1986 European Pat. Off. ...... 558/257
199658 10/1986 European Pat. Off. ...... 558/257
0219343 4/1987 European Pat. Off. ...... 558/257

OTHER PUBLICATIONS

Iwataki et al., Advances in Pesticide Science, Part 2, Geissbuhler (Ed.) Pergemn Press (1978), pp. 235–243.

Primary Examiner—Mary C. Lee
Assistant Examiner—Robert C. Whittenbaugh
Attorney, Agent, or Firm—Keil & Weinkauf

[57] ABSTRACT

Cyclohexenone compounds of the formula I

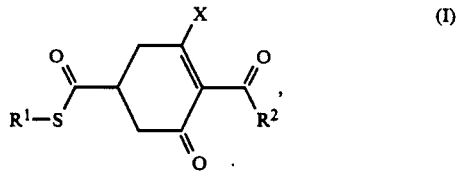

wherein $R^1$, $R^2$, A and X have the meanings given in the disclosure and claims, their preparation and their use as growth-regulating agents or herbicides.

5 Claims, No Drawings

CYCLOHEXENONE COMPOUNDS AND USE AS HERBICIDES OR AS PLANT GROWTH REGULATORS

This application is a continuation-in-part of U.S. patent application Ser. No. 07/240,465, filed Sept. 2, 1988 now abandoned, which is a continuation-in-part of Ser. No. 07/201,891, filed Jun. 3, 1988 now abandoned.

The herbicidal action of cyclohexenone compounds which contain an oxime ether group in the 2-position of the side chain are known (U.S. Pat. No. 4,249,937; CA No. 1 205 813; Adv. Pest. Science, Part 2, Pergamon Press, Zurich, 1978; E. H. Geissbühler, Proc. 4th Intern. Congress of Pesticide Chemistry (IUPAC), 1978, 235). It is also known that certain 2-acyl-3-hydroxy-cyclohex-2-en-1-ones regulate plant growth (U.S. Pat. Nos. 4,560,403, 4,584,013, 4,640,706, EP-A-177 450 and EP-A-199 658).

We have found novel cyclohexenone compounds of the formula I

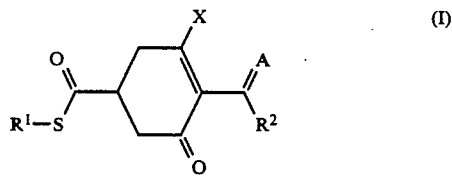

where $R^1$ is hydrogen; $C_1-C_6$-alkyl which is unsubstituted or substituted by $C_1-C_4$-alkoxy, $C_1-C_4$-alkylthio, $C_1-C_4$-dialkylamino, hydroxyl or halogen; $C_1-C_6$-alkenyl; $C_3-C_6$-cycloalkyl; or phenyl or benzyl which is unsubstituted or substituted by halogen, $C_1-C_4$-alkyl, $C_1-C_4$-alkoxy or nitro, $R^2$ is $C_1-C_4$-alkyl or cyclopropyl, A is oxygen; a radical $NOR^3$, where $R^3$ is $C_1-C_4$-alkyl, $C_3$- or $C_4$-alkenyl, $C_3$- or $C_4$-alkynyl, $C_2-C_4$-haloalkyl, $C_3$- or $C_4$-haloalkenyl or $C_2-C_4$-alkoxyalkyl; or a radical $NR^4$, where $R^4$ is hydrogen, $C_1-C_6$-alkyl, $C_1-C_4$-hydroxyalkyl, $C_1-C_4$-alkoxyalkyl, benzyl or phenyl, X is hydroxyl; chlorine; $C_1-C_6$-alkylthio which is unsubstituted or substituted by $C_1-C_4$-alkoxy, $C_1-C_4$-alkylthio, $C_1-C_4$-dialkylamino, hydroxyl or halogen; $C_1-C_6$-alkenylthio; $C_3-C_6$-cycloalkylthio; or phenylthio or benzylthio which is unsubstituted or substituted by halogen, $C_1-C_4$-alkoxy or nitro. The invention also encompasses the agriculturally useful salts of the compounds of the formula I.

Cyclohexenone compounds of the formula I where A is a radical $NOR^3$ have advantageous herbicidal activity against species from the grass family (gramineae).

Cyclohexenone compounds of the formula I in which A is oxygen or $NR^4$ have particularly advantageous growth-regulating properties, for example stalk-shortening properties.

In formula I, $R^1$ is, for example, hydrogen, methyl, ethyl, n-hexyl, isopropyl, tert-butyl, allyl, 2-methoxyethyl, 2-ethylthioethyl, 3-chloropropyl, 2-dimethylaminoethyl, 2-hydroxyethyl, cyclohexyl, benzyl, 4-methylbenzyl, 4-chlorobenzyl, phenyl, p-tolyl, 4-chlorophenyl, 4-methoxyphenyl or 3-nitrophenyl, preferably methyl, ethyl, phenyl or 4-chlorophenyl.

In formula I, $R^2$ is, for example, methyl, ethyl, n-propyl, isopropyl, n-butyl or cyclopropyl.

If, in formula I, A is a group $NOR^3$, $R^3$ is, for example, ethyl, propyl, allyl, (E)-but-2-en-1-yl, propargyl, but-2-yn-1-yl, (E)-3-chloroprop-2-en-1-yl or 2-methoxyethyl.

If, in formula I, A is a group $NR^4$, $R^4$ is, for example, hydrogen, methyl, ethyl, propyl, isopropyl, n-butyl, n-hexyl, allyl, 2-hydroxyethyl, 2-methoxyethyl, benzyl or phenyl.

In formula I, X is, for example, hydroxyl, chlorine, methylthio, ethylthio, n-hexylthio, isopropylthio, tert-butylthio, allylthio, 2-methoxyethylthio, 2-ethylthioethylthio, 3-chloropropylthio, 2-dimethylaminoethylthio, 2-hydroxyethylthio, cyclohexylthio, benzylthio, 4-methylbenzylthio, 4-chlorobenzylthio, phenylthio, p-tolylthio, 4-chlorophenylthio, 4-methoxyphenylthio or 3-nitrophenylthio. Preferred compounds are those in which X is hydroxyl, chlorine, methylthio, ethylthio, phenylthio or 4-chlorophenylthio.

Suitable salts of compounds of the formula I are agriculturally useful salts, e.g., alkali metal salts, especially the potassium and sodium salts, alkaline earth metal salts, especially the calcium, magnesium and barium salts, manganese, copper, zinc and iron salts, and ammonium, phosphonium, sulfonium or sulfoxonium salts, e.g., ammonium salts, tetraalkylammonium salts, benzyltrialkylammonium salts, trialkylsulfonium salts and trialkylsulfoxonium salts.

The novel cyclohexenone compounds may be obtained, for example, if a corresponding carboxylic acid of the formula II

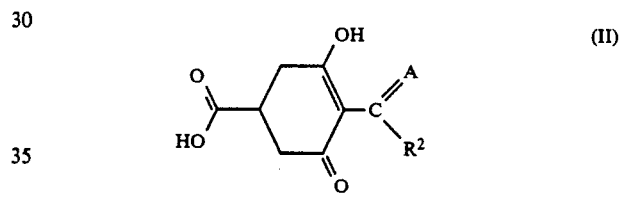

is first reacted with a chlorinating agent in the presence or absence of a base at from $-10°$ to $+120°$ C., preferably from $20°$ to $80°$ C. In this reaction, exchange of the two hydroxyl groups for chlorine takes place preferentially, i.e. faster, at the side (carboxyl) group, while the hydroxyl group on the cyclohexenone ring system is exchanged more slowly, regardless of the chlorinating agent. This makes it possible to obtain a fairly wide variety of compounds, in particular cyclohexenone compounds which carry unchanged hydroxyl on the ring.

The same applies regarding the subsequent reaction, i.e. exchange of the chlorine. In this case too, exchange takes place more rapidly at the acid chloride than at the ring.

The chlorinating agent used is one of the conventional ones, for example an inorganic or organic acid chloride, such as thionyl chloride, phosgene, phosphorus oxychloride, phosphorus pentachloride or oxalyl chloride.

A suitable base is a tertiary amine base, such as triethylamine, tributylamine, tri-2-ethylhexylamine, N,N-dimethylaminocyclohexane or pyridine. Tricarbonyl compounds and halogenating agents are used in a molar ratio of from 1:1 to 1:20, i.e. the chlorinating agent is used in excess for economic reasons.

Where the reaction is carried out in the presence of a base, the latter is added in excess, for example from 1 to 20 moles per mole of the compound.

In some cases, it may be advantageous to carry out the reaction in the presence of an inert diluent, for example benzene, toluene, chloroform, dichloromethane, 1,2-dichloroethane, dioxane, tetrahydrofuran, N,N-dimethylformamide or N-methylpyrrolidone.

The reaction is complete after a few hours. Evaporating down the solution generally gives the acid chloride III

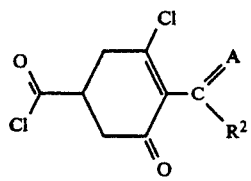

which can be reacted, without further isolation, with an appropriate thiol $R^1$-SH to give a compound of the formula I.

This reaction is advantageously carried out in the presence of a tertiary amine base, for example triethylamine, N,N-dimethylaminocyclohexane or pyridine.

The acid chloride III and the thiol $R^1$-SH are used in a molar ratio of 1:1 to 1:20, once again for economic reasons. If the reaction is carried out in the presence of a base, the latter is likewise added in excess, based on the acid chloride.

The substitution reaction can also be carried out in the presence of an inert diluent, for example benzene, toluene, chloroform, dichloromethane, 1,2-dichloroethane, dioxane, tetrahydrofuran, N,N-dimethylformamide or N-methylpyrrolidone.

The reaction is complete after a few hours, after which the reaction product can be obtained by evaporating down the reaction solution, taking up the residue in methylene chloride and extracting the solution by shaking with dilute sodium carbonate solution and water. After removal of the solvent, the resulting crude product can be purified by column chromatography over silica gel.

The active ingredients can be used as such, in the form of their formulations or in the application forms prepared from these, for example in the form of directly sprayable solutions, powders, suspensions or dispersions, emulsions, oil dispersions, pastes, dusting agents, broadcasting agents or granules, by spraying, atomizing, dusting, broadcasting or watering. The application forms depend entirely on the intended uses; they should in any case ensure very fine distribution of the active ingredients according to the invention.

Directly sprayable solutions, emulsions, pastes or oil dispersions can be prepared using mineral oil fractions having a medium to high boiling point, such as kerosine or diesel oil, as well as coal tar oils and vegetable or animal oils, aliphatic, cyclic and aromatic hydrocarbons, e.g. benzene, toluene, xylene, paraffin, tetrahydronaphthalene, alkylated naphthalenes or their derivatives, e.g. methanol, ethanol, propanol, butanol, chloroform, carbon tetrachloride, cyclohexanol, cyclohexanone, chlorobenzene, isophorone and strongly polar solvents, e.g. dimethylformamide, dimethyl sulfoxide, N-methylpyrrolidone or water.

Aqueous application forms can be prepared from emulsion concentrates, pastes or wettable powders (spray powders or oil dispersions) by adding water. To prepare emulsions, pastes or oil dispersions, the substances as such or dissolved in an oil or solvent can be homogenized in water by means of wetting agents, spreader-stickers, dispersants or emulsifiers. It is also possible to prepare concentrates consisting of the active ingredient, wetting agents, adhesion promoters, dispersants or emulsifiers and, if required, solvent or oil, these concentrates being suitable for dilution with water.

Suitable surfactants are alkali metal, alkaline earth metal and ammonium salts of ligninsulfonic acid, naphthalenesulfonic acid, phenolsulfonic acid, alkylarylsulfonates, alkylsulfates, alkylsulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols or octadecanols, salts of sulfated fatty alcohol glycol ethers, condensates of sulfonated naphthalene and naphthalene derivatives with formaldehyde, condensates of naphthalene and of naphthalenesulfonic acid with phenol and formaldehyde, polyoxyethylene octylphenol ether, oxyethylated isooctylphenyl, octylphenol, nonylphenol, alkylphenol polyglycol ether, tributylphenyl polyglycol ether, alkylaryl polyether alcohols, isotridecyl alcohol, fatty alcohol/ethylene oxide condensates, oxyethylated castor oil, polyoxyethylene alkyl ethers, oxyethylated polyoxypropylene, lauryl alcohol polyglycol ether acetal, sorbitol esters, ligninsulfite waste liquors and methylcellulose.

Powders, broadcasting agents and dusting agents can be prepared by mixing or milling the active ingredients together with a solid carrier.

Granules, for example coated granules, impregnated granules and homogeneous granules, can be prepared by binding the active ingredients to solid carriers. Examples of solid carriers are mineral earths, such as silica gel, silicas, silicates, talc, kaolin, attaclay, limestone, lime, chalk, bole, loess, clay, dolomite, diatomaceous earth, calcium sulfate, magnesium sulfate, magnesium oxide, ground plastics, fertilisers, e.g. ammonium sulfate, ammonium phosphate, ammonium nitrate or ureas, and vegetable products, such as cereal flour, ground bark, sawdust and nutshell meal, cellulose powder and other solid carriers.

The formulations contain in general from 0.1 to 95, preferably from 0.5 to 90, % by weight of active ingredient.

The concentrations of active ingredients in the ready-to-use formulations can be varied within fairly wide ranges.

In general, they are from 0.0001 to 10%, preferably from 0.0001 to 1%.

The application rate of the active ingredient is from 0.001 to 1, preferably from 0.01 to 0.1, kg/ha in the open.

Oils of various types, other herbicides and growth regulators, fungicides, pesticides, and bactericides can be added to the active ingredients, if necessary only directly before use (tank mix). These agents can be mixed with the novel agents in a weight ratio of 1:10 to 10:1.

The cyclohexenone derivatives of the formula I (where A is oxygen or $NR^4$) can influence virtually all development stages of a plant in different ways and are therefore used as growth regulators. The variety of actions of the plant growth regulators depends in particular (a) on the plant species and variety,
(b) on the time of application, relative to the development stage of the plant, and on the season, (c) on the site and method of application, for example seed dressing, soil treatment, leaf application or stem injection in the case of trees, (d) on climatic factors, e.g. temperature and amount of precipitation, as well as length of day and intensity of light, (e) on the nature of the soil (including fertilizer application), (f) on the formulation and application form of the active ingredient and finally (g) on the concentrations of active ingredient which are used.

From the large number of different methods of application of the novel plant growth regulators in crop cultivation, in agriculture and in horticulture, a few are mentioned below.

A. With the compounds which can be used according to the invention, the vegetative growth of the plants can be greatly inhibited, this being evident in particular in a reduction in lengthwise growth. The treated plants accordingly exhibit suppressed growth, and furthermore a dark leaf coloration is observed.

A practical advantage is reduced intensity of growth of grasses in street edges, hedgerows, canal banks and grassed areas such as parks, sports areas, orchards, lawns and airfields, so that the costly and labor-intensive cutting of grass can be reduced.

Also of economic interest is the increase in the stability of crops which are susceptible to lodging, such as cereals, corn, sunflowers and soybeans. The resulting shortening and strengthening of stalks reduces or eliminates the danger of lodging (bending) of plants under unfavorable weather conditions prior to harvesting.

The use of growth regulators in cotton for inhibiting growth in length and for changing the time of ripening is also important. This permits completely mechanized harvesting of this important crop.

By using growth regulators, lateral branching of the plants can be increased or inhibited. This is of interest if it is intended to inhibit the formation of side shoots (suckers) in favor of leaf growth, for example in tobacco plants.

Growth regulators can also be used for substantially increasing frost resistance, for example in winter rape. On the one hand, this inhibits the growth in length and the development of a leaf or plant mass which is too luxuriant (and hence particularly susceptible to frost). On the other hand, the young rape plants are kept in the vegetative stage of development after sowing and before the onset of winter frosts, despite advantageous growth conditions. This also eliminates the danger of frost in the case of plants which tend to premature loss of inhibition of flowering and to go over into the generative phase. In other crops too, for example winter cereals, it is advantageous if, as a result of treatment with novel compounds in the fall, the crops are well tillered but not too luxuriant at the beginning of winter. This makes it possible to prevent increased sensitivity to frost and, owing to the relatively small leaf and plant mass, attack by various diseases (e.g. fungal disease). Inhibition of vegetative growth also permits denser planting of the soil in many crops, so that it is possible to achieve an increased yield, based on the soil area.

B. Using the growth regulators, it is possible to achieve increased yields of both parts of plants and plant ingredients. For example, it is possible to induce the growth of larger amounts of buds, flowers, leaves, fruit, seeds, roots and tubers, to increase the content of sugar in sugar beet, sugar cane and citrus fruit, to increase the protein content of cereals or soybean, or to stimulate rubber trees to produce greater latex flow.

The cyclohexenone derivatives of the formula I (where A is oxygen or $NR^4$) can increase yields by intervening in the plant metabolism or by promoting or inhibiting the vegetative and/or generative growth.

C. Finally, plant growth regulators can shorten or lengthen the development stages as well as accelerate or delay ripening of the harvested plant parts before or after harvesting.

For example, facilitating harvesting is also of economic interest, this being permitted by unusing citrus fruit, olives or other species and varieties of pomes, drupes and dry indehiscent fruit to fall at a specific time or by reducing the adhesion to the tree. The same mechanism, i.e. promotion of the formation of abscission tissue between the fruit or leaf part and shoot part of the plant, is also important for easily controllable defoliation of crop plants.

D. Growth regulators can also be used to reduce the water consumption of plants. This is particularly important for agricultural areas which have to be irrigated at great expense, for example in arid or semiarid areas. By using the novel substances, the intensity of irrigation can be reduced, making cultivation more economical. Growth regulators result in better utilization of the existing water because, inter alia, the extent of opening of the stomata is reduced, a thicker epidermis and cuticule are formed, penetration of the roots through the soil is improved and the microclimate in the crop is advantageously influenced by more compact growth.

The active ingredients of the formula I (where A is oxygen or $NR^4$) which are to be used according to the invention can be fed to the crops both via the seed (as seed dressings) and via the soil, i.e. through the roots and, particularly preferably, via the leaves by spraying.

Because of the good toleration by plants, the application rate can be varied greatly.

In the case of seed treatment, amounts of active ingredient of in general from 0.001 to 50, preferably from 0.01 to 10, g per kg of seed are required.

For leaf and soil treatment, doses of from 0.01 to 5, preferably from 0.05 to 2, kg/ha are generally regarded as sufficient.

Simultaneously with the reduction in growth in length, there was also an increase in the intensity of color of the leaves. The increased chlorophyll content is expected also to result in a higher photosynthesis rate and hence an increased yield.

The compounds of the formula I in which A is $NOR^3$ are, as mentioned above, powerful growth inhibitors and can therefore be used as herbicides.

The agents which contain these active ingredients can be applied by the pre-emergence or post-emergence method. If the active ingredients are less well tolerated by certain crops, it is also possible to use application techniques where the herbicides are sprayed using sprayers in such a way that the leaves of the sensitive crops are avoided while the active ingredients reach the leaves of undesirable plants growing underneath or the bare soil surface (post-directed, lay-by).

The application rates of the active ingredient are from 0.25 to 5, preferably from 0.5 to 3, kg/ha, depending on the method of application, the season, the target plants and the stages of growth.

In view of the action spectrum of weeds controlled, the toleration by crops or the desirable effect on crop growth and in view of the wide variety of application methods, the novel compounds can be used in a large number of crops.

To broaden the action spectrum and to achieve synergistic effects, the active ingredients of the formula I can be mixed both with one another and with a large number of other herbicidal or growth-regulating active ingredients and applied together. Examples of suitable components for the mixture are diazines, 4H-3,1-benzoazine derivatives, benzothiadiazinones, 2,6-dinitroanilines, N-phenylcarbamates, thiocarbamates, halocarboxylic acids, triazines, amides, ureas, diphenyl ethers, cyclohexenone compounds, triazinones, uracils, benzofuran derivatives, quinolinecarboxylic acids and others.

It may also be useful to apply the active ingredients of the formula I, alone or in combination with other herbicides, mixed with further crop protection agents, for example with agents for controlling pests or phytopathogenic fungi or bacteria. The miscibility with mineral salt solutions, which are used for eliminating nutrient and trace element deficiencies, is also of interest. Non-phytotoxic oils and oil concentrates may also be added.

PREPARATION EXAMPLE 10.0 g of 2-butyrylcyclohexane-1,3-dione-5-carboxylic acid are stirred with 80 ml of oxalyl chloride at 25° C. for 16 h. The solution is evaporated down and the residue is dissolved in 120 ml of tetrahydrofuran. A solution of 8.9 g of triethylamine and 5.5 g of ethanethiol in 20 ml of tetrahydrofuran is added dropwise at 0° C. The mixture is stirred for 3 h and then evaporated down, and the residue is extracted by shaking with dichloromethane/water and evaporated down. Chromatography over silica gel gives 10.1 g of 2-butyryl-3-ethylthio-5-ethylthiocarbonylcyclohex-1-en-3-one as an oil (compound no. 33).

For example, the following compounds listed in Tables 1 to 6 can be obtained by appropriately modifying the above method, i.e. from appropriate raw materials.

TABLE 1

| Compound no. | $R^1$ | $R^2$ | X | M.p. (°C.) |
|---|---|---|---|---|
| 1 | H | n-$C_3H_7$ | OH | |
| 2 | $CH_3$ | n-$C_3H_7$ | OH | 66–68 |
| 3 | $C_2H_5$ | n-$C_3H_7$ | OH | resin |
| 4 | n-$C_6H_{13}$ | n-$C_3H_7$ | OH | |
| 5 | H | $C_2H_5$ | OH | |
| 6 | $CH_3$ | $C_2H_5$ | OH | 79–81 |
| 7 | $C_2H_5$ | $C_2H_5$ | OH | 63–65 |
| 8 | n-$C_6H_{13}$ | $C_2H_5$ | OH | |
| 9 | H | cyclopropyl | OH | |
| 10 | $CH_3$ | cyclopropyl | OH | |
| 11 | $C_2H_5$ | cyclopropyl | OH | |
| 12 | n-$C_6H_{13}$ | cyclopropyl | OH | |
| 13 | $C_2H_5$ | $CH_3$ | OH | 53–55 |
| 14 | H | n-$C_3H_7$ | Cl | |
| 15 | $CH_3$ | n-$C_3H_7$ | Cl | |
| 16 | $C_2H_5$ | n-$C_3H_7$ | Cl | |
| 17 | n-$C_6H_{13}$ | n-$C_3H_7$ | Cl | |
| 18 | H | $C_2H_5$ | Cl | |
| 19 | $CH_3$ | $C_2H_5$ | Cl | 82–84 |
| 20 | $C_2H_5$ | $C_2H_5$ | Cl | |
| 21 | n-$C_6H_{13}$ | $C_2H_5$ | Cl | |
| 22 | H | cyclopropyl | Cl | |
| 23 | $CH_3$ | cyclopropyl | Cl | |
| 24 | $C_2H_5$ | cyclopropyl | Cl | |
| 25 | n-$C_6H_{13}$ | cyclopropyl | Cl | |
| 26 | $C_2H_5$ | $CH_3$ | Cl | |
| 27 | t-$C_4H_9$ | n-$C_3H_7$ | OH | resin |
| 28 | $CH_3$ | phenyl | Cl | 98–100 |
| 29 | $CH_3$ | $C_2H_5$ | $NHC_3H_7$ | 68–70 |
| 30 | $CH_2CH_2OCH_3$ | $CH_3$ | OH | resin |
| 31 | $CH_3$ | $CH_3$ | OH | 69–71 |
| 32 | $CH_2CH_2OCH_3$ | $C_2H_5$ | OH | resin |
| 33 | $CH_2CH=CH_2$ | $C_2H_5$ | OH | resin |
| 34 | benzyl | n-$C_3H_7$ | OH | resin |
| 35 | $C_2H_5$ | $C_4H_9$ | OH | resin |
| 38 | t-$C_4H_9$ | $C_2H_5$ | OH | 99–101 |
| 39 | benzyl | $C_2H_5$ | OH | 56–57 |

TABLE 2

| Compound no. | $R^1$ | $R^2$ | M.p. (°C.) |
|---|---|---|---|
| 40 | $CH_3$ | $CH_3$ | 62–63 |
| 41 | $CH_3$ | $C_2H_5$ | 92–94 |
| 42 | $CH_3$ | n-$C_3H_7$ | 79–80 |
| 43 | $CH_3$ | n-$C_4H_9$ | 73–74 |
| 44 | $C_2H_5$ | $CH_3$ | |
| 45 | $C_2H_5$ | $C_2H_5$ | 77–78 |
| 46 | $C_2H_5$ | n-$C_3H_7$ | oil |
| 47 | $C_2H_5$ | n-$C_4H_9$ | |
| 48 | $C_2H_5$ | cyclopropyl | |
| 49 | n-$C_6H_{13}$ | n-$C_3H_7$ | oil |
| 50 | $CH_2=CH-CH_2$ | $C_2H_5$ | |
| 51 | $CH_2=CH-CH_2$ | n-$C_3H_7$ | oil |
| 52 | $(CH_3)_2CH$ | n-$C_3H_7$ | |
| 53 | $(CH_3)_2CH$ | $C_2H_5$ | 39–42 |
| 54 | $(CH_3)_3C$ | n-$C_3H_7$ | |
| 55 | $CH_3OCH_2CH_2$ | $C_2H_5$ | |
| 56 | $CH_3OCH_2CH_2$ | n-$C_3O_7$ | oil |
| 57 | $ClCH_2CH_2CH_2$ | $C_2H_5$ | |
| 58 | $ClCH_2CH_2CH_2$ | n-$C_3H_7$ | |
| 59 | $(CH_3)_2NCH_2CH_2$ | $C_2H_5$ | |
| 60 | $(CH_3)_2NCH_2CH_2$ | n-$C_3H_7$ | |
| 61 | cyclohexyl | n-$C_3H_7$ | |
| 62 | benzyl | n-$C_3H_7$ | |
| 63 | 4-methylbenzyl | n-$C_3H_7$ | |
| 64 | 4-chlorobenzyl | n-$C_3H_7$ | |
| 65 | phenyl | n-$C_3H_7$ | |
| 66 | 4-methylphenyl | n-$C_3H_7$ | |
| 67 | 4-chlorophenyl | n-$C_3H_7$ | |
| 68 | 4-methoxyphenyl | n-$C_3H_7$ | |
| 69 | 3-nitrophenyl | n-$C_3H_7$ | |
| 70 | benzyl | $C_2H_5$ | 112–114 |
| 71 | $CH_3$ | $CH_2CH_2CH_2Cl$ | 70–72 |
| 72 | $CH_3$ | phenyl | 139–140 |
| 73 | $CH_3$ | cyclopropyl | 103–104 |

TABLE 2-continued

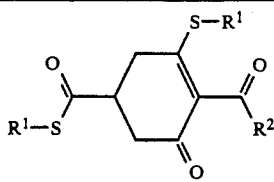

| Compound no. | $R^1$ | $R^2$ | M.p. (°C) |
|---|---|---|---|
| 74 | $CH_3$ | $CH_2OCH_3$ | 79–81 |

TABLE 3

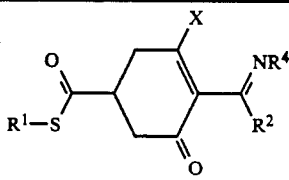

| Compound no. | $R^1$ | $R^2$ | $R^4$ | X | M.p. (°C) |
|---|---|---|---|---|---|
| 75 | $C_2H_5$ | $n-C_3H_7$ | H | OH | |
| 76 | $C_2H_5$ | $n-C_3H_7$ | $n-C_3H_7$ | OH | 36–38 |
| 77 | $C_2H_5$ | $n-C_3H_7$ | $HOCH_2CH_2$ | OH | |
| 78 | $C_2H_5$ | $n-C_3H_7$ | $CH_3OCH_2CH_2$ | OH | |
| 79 | $C_2H_5$ | $n-C_3H_7$ | $C_6H_5$ | OH | |
| 80 | $C_2H_5$ | $n-C_3H_7$ | $C_6H_5-CH_2$ | OH | |
| 81 | $C_2H_5$ | $n-C_3H_7$ | H | Cl | |
| 82 | $C_2H_5$ | $n-C_3H_7$ | $n-C_3H_7$ | Cl | |
| 83 | $C_2H_5$ | $n-C_3H_7$ | $HOCH_2CH_2$ | Cl | |
| 84 | $C_2H_5$ | $CH_3$ | $n-C_3H_7$ | OH | 76–78 |
| 85 | $CH_3$ | $C_2H_5$ | $i-C_3H_7$ | OH | 72–74 |
| 86 | benzyl | $C_2H_5$ | $n-C_3H_7$ | OH | 42–46 |
| 87 | ethyl | cyclopropyl | $n-C_3H_7$ | OH | |

TABLE 4

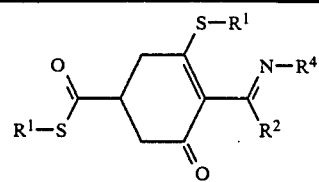

| Compound no. | $R^1$ | $R^2$ | $R^4$ |
|---|---|---|---|
| 88 | H | $n-C_3H_7$ | $n-C_3H_7$ |
| 89 | $CH_3$ | $n-C_3H_7$ | $n-C_3H_7$ |
| 90 | $C_2H_5$ | $n-C_3H_7$ | H |
| 91 | $C_2H_5$ | $n-C_3H_7$ | $n-C_3H_7$ |
| 92 | $C_2H_5$ | $n-C_3H_7$ | $HO-CH_2CH_2$ |
| 93 | $C_2H_5$ | $n-C_3H_7$ | $CH_3OCH_2CH_2$ |
| 94 | $C_2H_5$ | $n-C_3H_7$ | $C_6H_5$ |
| 95 | $C_2H_5$ | $n-C_3H_7$ | $C_6H_5-CH_2$ |
| 96 | $C_2H_5$ | $n-C_3H_7$ | $CH_2=CH-CH_2$ |
| 97 | $C_2H_5$ | $C_2H_5$ | H |
| 98 | $C_2H_5$ | $C_2H_5$ | $n-C_3H_7$ |
| 99 | $C_2H_5$ | $C_2H_5$ | $HOCH_2CH_2$ |
| 100 | $C_2H_5$ | $C_2H_5$ | $CH_3OCH_2CH_2$ |
| 101 | $C_2H_5$ | $C_2H_5$ | $CH_2=CH-CH_2$ |
| 102 | $n-C_6H_{13}$ | $n-C_3H_7$ | H |
| 103 | $n-C_6H_{13}$ | $n-C_3H_7$ | $n-C_3H_7$ |
| 104 | $CH_2=CH-CH_2$ | $n-C_3H_7$ | H |
| 105 | $CH_2=CH-CH_2$ | $n-C_3H_7$ | $n-C_3H_7$ |
| 106 | $(CH_3)_2CH$ | $n-C_3H_7$ | H |
| 107 | $(CH_3)_2CH$ | $n-C_3H_7$ | $n-C_3H_7$ |
| 108 | $(CH_3)_3C$ | $n-C_3H_7$ | H |
| 109 | $(CH_3)_3C$ | $n-C_3H_7$ | $n-C_3H_7$ |
| 110 | $CH_3OCH_2CH_2$ | $n-C_3H_7$ | H |

TABLE 5

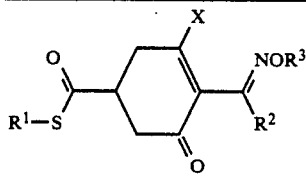

| Compound no. | $R^1$ | $R^2$ | $R^3$ | X | M.p. (°C) |
|---|---|---|---|---|---|
| 111 | H | $C_2H_5$ | $C_2H_5$ | OH | |
| 112 | H | $n-C_3H_7$ | $C_2H_5$ | OH | |
| 113 | $CH_3$ | $C_2H_5$ | $C_2H_5$ | OH | 76–78 |
| 114 | $CH_3$ | $n-C_3H_7$ | $C_2H_5$ | OH | |
| 115 | $C_2H_5$ | $C_2H_5$ | $C_2H_5$ | OH | resin |
| 116 | $C_2H_5$ | $n-C_3H_7$ | $C_2H_5$ | OH | |
| 117 | $C_2H_5$ | cyclopropyl | $C_2H_5$ | OH | |
| 118 | $C_2H_5$ | $C_2H_5$ | $CH_2=CH-CH_2$ | OH | |
| 119 | $C_2H_5$ | $n-C_3H_7$ | $CH_2=CH-CH_2$ | OH | |
| 120 | $C_2H_5$ | $C_2H_5$ | $E-(ClCH=CH-CH_2)$ | OH | |
| 121 | $C_2H_5$ | $n-C_3H_7$ | $E-(ClCH=CH-CH_2)$ | OH | 39–41 |
| 122 | $C_2H_5$ | $C_2H_5$ | $E-(CH_3CH=CH-CH_2)$ | OH | |
| 123 | $C_2H_5$ | $n-C_3H_7$ | $E-(CH_3CH=CH-CH_2)$ | OH | 32–34 |
| 124 | $n-C_6H_{13}$ | $n-C_3H_7$ | $C_2H_5$ | OH | |
| 125 | $CH_2=CH-CH_2$ | $n-C_3H_7$ | $C_2H_5$ | OH | |
| 126 | $CH_3OCH_2CH_2$ | $n-C_3H_7$ | $C_2H_5$ | OH | resin |
| 127 | benzyl | $n-C_3H_7$ | $C_2H_5$ | OH | |
| 128 | 4-chlorobenzyl | $n-C_3H_7$ | $C_2H_5$ | OH | |
| 129 | phenyl | $n-C_3H_7$ | $C_2H_5$ | OH | |
| 130 | 4-chlorophenyl | $n-C_3H_7$ | $C_2H_5$ | OH | |
| 131 | 4-methoxyphenyl | $n-C_3H_7$ | $C_2H_5$ | OH | |
| 132 | 3-nitrophenyl | $n-C_3H_7$ | $C_2H_5$ | OH | |
| 133 | $C_2H_5$ | $n-C_3H_7$ | $HC{\equiv}C$ | OH | |
| 134 | $C_2H_5$ | $n-C_3H_7$ | $CH_3-C{\equiv}C$ | OH | |
| 135 | $C_2H_5$ | $n-C_3H_7$ | $ClCH_2CH_2$ | OH | |

TABLE 5-continued

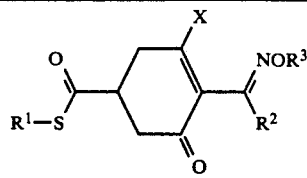

| Compound no. | R¹ | R² | R³ | X | M.p. (°C.) |
|---|---|---|---|---|---|
| 136 | $C_2H_5$ | n-$C_3H_7$ | $CH_3OCH_2CH_2$ | OH | |
| 137 | $C_2H_5$ | n-$C_3H_7$ | $C_2H_5$ | Cl | |
| 138 | $C_2H_5$ | n-$C_3H_7$ | E-(ClCH=CH—$CH_2$) | Cl | |
| 139 | $C_2H_5$ | n-$C_3H_7$ | E-($CH_3$CH=CH—$CH_2$) | Cl | |
| 140 | $CH_3$ | $CH_3$ | E-(ClCH=CH$CH_2$) | OH | 67–68 |
| 141 | $CH_3$ | $C_2H_5$ | $C_2H_5$ | OH | 58–60 |
| 142 | benzyl | $C_2H_5$ | $C_2H_5$ | OH | 39–42 |
| 143 | benzyl | $C_3H_7$ | E-(ClCH=CH—$CH_2$) | OH | resin |
| 144 | ethyl | cyclopropyl | E-(ClCH=CH—$CH_2$) | OH | |

TABLE 6

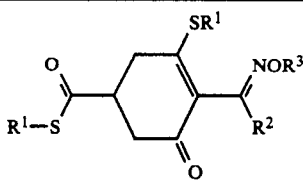

| Compound no. | R¹ | R² | R³ | M.p. (°C.) |
|---|---|---|---|---|
| 145 | $CH_3$ | $C_2H_5$ | $C_2H_5$ | |
| 146 | $CH_3$ | n-$C_3H_7$ | $C_2H_5$ | |
| 147 | $C_2H_5$ | $C_2H_5$ | $C_2H_5$ | |
| 148 | $C_2H_5$ | n-$C_3H_7$ | $C_2H_5$ | resin |
| 149 | $C_2H_5$ | $C_2H_5$ | E-(ClCH=CH—$CH_2$) | |
| 150 | $C_2H_5$ | n-$C_3H_7$ | E-(ClCH=CH—$CH_2$) | |
| 151 | $CH_2CH_2OCH_3$ | n-$C_3H_7$ | OH | resin |

The cyclohexenone derivatives of the formula I can influence virtually all stages of development of a plant in many ways and are therefore used as growth regulators.

To determine the growth-regulating properties of the test substances, test plants were grown on a substrate adequately supplied with nutrients, in plastic vessels (about 12.5 cm diameter, volume about 500 ml).

In the case of soil treatments, the test substances, in the form of aqueous formulations, were poured onto the substrate either on the day of sowing (pre-emergence method) or after germination (post-emergence method).

In the case of leaf application, the substances to be tested, in the form of aqueous formulations, were sprayed onto the plants (post-emergence leaf treatment).

The comparative substances used were the known, commercial growth regulator chlormequat chloride (A). Examples nos. 13 (D) and 15 (B) of EP-A-123 001 and 6-Acetamido-4-trifluoromethylsulfonamido-1,3-xylene (C, common name "mefluidide").

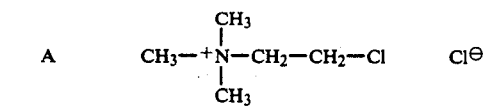

B  3,5-Dioxo-4-butyrylcyclohexane-carboxylic acid ethyl ester
C  6-Acetamido-4-trifluoromethylsulfonamido-1,3-xylene
D  3,5-Dioxo-4-butyrylcyclohexane-carboxylic acid The growth-regulating action observed was proved by measuring the growth in height at the end of the experiment. The measured values thus obtained were expressed as a ratio of the growth in height of the untreated plants. Parallel with the reduction of growth in length, there was an increase in the colour intensity of the leaves. The increased chlorophyll content is likely also to result in an increased photosynthesis rate and hence an increased yield.

The specific data are shown in Tables 1 to 14 below:

TABLE 1

Summer wheat, "Kolibri" variety
Post-emergence leaf treatment

| Compound No. | Concentration mg a.i./vessel | Rel. growth height |
|---|---|---|
| | Experiment I | |
| Untreated | — | 100 |
| A | 6 | 75.1 |
| 7 | 6 | 67.0 |
| 71 | 6 | 72.3 |
| | Experiment II | |
| Untreated | — | 100 |
| A | 0.38 | 85.3 |
| B | 0.38 | 73.8 |
| 13 | 0.38 | 64.5 |
| 30 | 0.38 | 66.8 |
| 31 | 0.38 | 70.3 |
| 32 | 0.38 | 68.0 |
| | Experiment III | |
| Untreated | — | 100 |
| CCC | 1.5 | 79.5 |
| | 6 | 75.1 |
| 33 | 1.5 | 67.8 |
| | 6 | 58.9 |

TABLE 2

Spring barley, "Aramir" variety
Pre-emergence soil treatment

| Compound No. | Concentration mg a.i./vessel | Rel. growth height |
|---|---|---|

TABLE 2-continued

| | Experiment I | |
|---|---|---|
| Untreated | — | 100 |
| A | 6 | 85.8 |
| B | 6 | 58.9 |
| 7 | 6 | 50.1 |
| 19 | 6 | 42.3 |
| | Experiment II | |
| Untreated | — | 100 |
| A | 6 | 72.4 |
| B | 6 | 65.2 |
| 6 | 6 | 54.3 |
| 31 | 6 | 59.7 |
| 32 | 6 | 52.5 |
| 33 | 6 | 57.9 |
| 38 | 6 | 54.3 |

TABLE 3

Spring barley, "Aramir" variety
Post-emergence leaf treatment

| Compound No. | Concentration mg a.i./vessel | Rel. growth height |
|---|---|---|
| Untreated | — | 100 |
| CCC | 1.5 | 97.6 |
| | 6 | 91.6 |
| 33 | 1.5 | 75.1 |
| | 6 | 61.6 |

TABLE 4

Spring barley, "Aramir" variety
Post-emergence leaf treatment

| Compound No. | Concentration mg a.i./vessel | Rel. growth height |
|---|---|---|
| | Experiment I | |
| Untreated | — | 100 |
| A | 6 | 87.0 |
| B | 6 | 78.7 |
| 53 | 6 | 70.8 |
| 7-Na-salt | 6 | 67.9 |
| | Experiment II | |
| Untreated | — | 100 |
| A | 0.1 | 95.4 |
| | 0.38 | 91.9 |
| | 1.5 | 89.5 |
| B | 0.1 | 89.5 |
| | 0.38 | 75.4 |
| | 1.5 | 60.1 |
| 2 | 0.1 | 84.8 |
| | 0.38 | 70.7 |
| | 1.5 | 54.2 |
| 6 | 0.1 | 78.9 |
| | 0.38 | 63.6 |
| | 1.5 | 51.8 |
| 7 | 0.1 | 82.4 |
| | 0.38 | 68.3 |
| | 1.5 | 58.9 |
| 13 | 0.1 | 78.9 |
| | 0.38 | 63.6 |
| | 1.5 | 53.0 |
| 30 | 0.1 | 80.1 |
| | 0.38 | 63.6 |
| | 1.5 | 56.5 |
| 31 | 0.1 | 75.4 |
| | 0.38 | 64.8 |
| | 1.5 | 53.0 |
| 32 | 0.1 | 80.1 |
| | 0.38 | 67.1 |
| | 1.5 | 54.2 |

TABLE 5

Rice, "Bahia" variety
Post-emergence soil treatment

| Compound No. | Concentration mg a.i./vessel | Rel. growth height |
|---|---|---|
| | Experiment I | |
| Untreated | — | 100 |
| A | 1.5 | 100 |
| B | 1.5 | 52.0 |
| 7 | 1.5 | 42.8 |
| | Experiment II | |
| Untreated | — | 100 |
| A | 1.5 | 94.3 |
| B | 1.5 | 82.3 |
| 2 | 1.5 | 69.0 |
| 6 | 1.5 | 50.4 |
| 13 | 1.5 | 66.4 |
| 30 | 1.5 | 63.7 |
| 31 | 1.5 | 55.8 |
| 32 | 1.5 | 58.4 |
| 33 | 1.5 | 61.1 |
| 38 | 1.5 | 74.3 |
| 39 | 1.5 | 66.4 |
| | Experiment III | |
| Untreated | — | 100 |
| A | 6 | 94.3 |
| B | 6 | 49.1 |
| 6 | 6 | 42.5 |
| 13 | 6 | 39.8 |
| 30 | 6 | 39.8 |
| 31 | 6 | 37.2 |
| 32 | 6 | 39.8 |
| 33 | 6 | 39.8 |
| 39 | 6 | 39.8 |

TABLE 6

Rice, "Bahia" variety
Post-emergence leaf treatment

| Compound No. | Concentration mg a.i./vessel | Rel. growth height |
|---|---|---|
| Untreated | — | 100 |
| A | 0.1 | 100 |
| | 0.4 | 100 |
| B | 0.1 | 86.9 |
| | 0.4 | 84.2 |
| 7 | 0.1 | 70.6 |
| | 0.4 | 50.3 |

TABLE 7

Rice, "Nihonbare"
Post-emergence leaf treatment

| Compound No. | Concentration mg a.i./vessel | Rel. growth height |
|---|---|---|
| Untreated | — | 100 |
| CCC | 1.5 | 100 |
| | 6 | 100 |
| 33 | 1.5 | 84.7 |
| | 6 | 73.7 |

TABLE 8

Sunflower, "Sorex" variety
Post-emergence leaf treatment

| Compound No. | Concentration mg a.i./vessel | Rel. growth height |
|---|---|---|
| | Experiment I | |
| Untreated | — | 100 |
| A | 6 | 88.3 |
| B | 6 | 87.6 |
| 7 | 6 | 77.0 |
| 40 | 6 | 78.6 |
| 41 | 6 | 77.0 |
| 51 | 6 | 75.4 |
| 53 | 6 | 78.6 |
| 56 | 6 | 80.2 |
| 71 | 6 | 78.6 |
| 7-Na-salt | 6 | 78.6 |
| | Experiment II | |
| Untreated | — | 100 |

TABLE 8-continued

| | | |
|---|---|---|
| A | 6 | 86.5 |
| B | 6 | 83.4 |
| 3 | 6 | 74.1 |
| 13 | 6 | 77.2 |
| 30 | 6 | 71.0 |
| 31 | 6 | 74.1 |
| 32 | 6 | 77.2 |
| 33 | 6 | 77.2 |
| 36 | 6 | 77.2 |

TABLE 9

Soje, "Maple Arrow" variety
Post-emergence leaf treatment

| Compound No. | Concentration mg a.i./vessel | Rel. growth height |
|---|---|---|
| Untreated | — | 100 |
| A | 0.5 | 86.8 |
| | 1.5 | 86.8 |
| 7 | 0.5 | 74.8 |
| | 1.5 | 70.0 |
| 53 | 0.5 | 85.6 |
| | 1.5 | 78.4 |

TABLE 10

Corn, "Inrakorn" variety
Post-emergence leaf treatment

| Compound No. | Concentration mg a.i./vessel | Rel. growth height |
|---|---|---|
| Untreated | — | 100 |
| A | 1.5 | 96.4 |
| B | 1.5 | 81.2 |
| 7 | 1.5 | 73.6 |

In further experiments, grasses and mixtures of grasses were grown in plastic vessels (surface area about 100 cm², on a substrate supplied with adequate amounts of nutrients. After the grass had been cut uniformly to about 5 cm in length, the substances to be tested, in the form of aqueous formulations, were sprayed onto the plants. The growth-regulating action observed was proved by measuring the shoots at the end of the experiment. The measured values thus obtained were expressed as a ratio of the growth in height of the untreated plants.

The specific data are shown in Tables 11 to 13

TABLE 11

Lawn, ("Berliner Tiergarten" mixture)
Post-emergence leaf treatment (after cutting)

| Compound No. | Concentration mg a.i./vessel | Rel. growth height |
|---|---|---|
| Experiment I | | |
| untreated | — | 100 |
| A | 1.5 | 96.8 |
| B | 1.5 | 85.5 |
| 2 | 1.5 | 71.0 |
| 3 | 1.5 | 77.4 |
| 6 | 1.5 | 58.1 |
| 7 | 1.5 | 76.0 |
| 13 | 1.5 | 77.4 |
| 30 | 1.5 | 71.0 |
| 31 | 1.5 | 64.5 |
| 32 | 1.5 | 61.3 |
| 34 | 1.5 | 77.4 |
| 36 | 1.5 | 77.4 |
| 38 | 1.5 | 71.0 |
| 39 | 1.5 | 71.0 |
| Experiment II | | |
| Untreated | — | 100 |
| CCC | 1.5 | 100 |
| | 6 | 100 |

TABLE 11-continued

| | | |
|---|---|---|
| 33 | 1.5 | 96.8 |
| | 6 | 87.1 |

TABLE 12

Rohrschwingel (Festuca arundinacea)
Post-emergence leaf treatment (after cutting)
Evaluation 20 days after treatment

| Compound No. | Concentration mg a.i./vessel | Rel. growth height |
|---|---|---|
| Untreated | — | 100 |
| C | 0.375 | 103 |
| | 0.750 | 95 |
| | 1.500 | 90 |
| 7 | 0.375 | 95 |
| | 0.750 | 68 |
| | 1.500 | 73 |

TABLE 13

Bermuda grass, (Cynodon dactylon)
Post-emergence leaf treatment (after cutting)
Evaluation 2 weeks after treatment

| Compound No. | Concentration mg a.i./vessel | Rel. growth height |
|---|---|---|
| Experiment I | | |
| Untreated | — | 100 |
| C | 0.75 | 103 |
| | 1.50 | 91 |
| 7 | 0.75 | 69 |
| | 1.50 | 53 |
| Experiment II | | |
| Untreated | — | 100 |
| Flurprimidol | 0.2 | 91 |
| | 1.0 | 67 |
| | 5.0 | 67 |
| 33 | 0.2 | 64 |
| | 1.0 | 67 |
| | 5.0 | 56 |
| Experiment III | | |
| Untreated | — | 100 |
| Mefluidide | 0.2 | 89 |
| | 1.0 | 78 |
| | 5.0 | 53* |
| 33 | 0.2 | 82 |
| | 1.0 | 76 |
| | 5.0 | 54 |

*Substantial leaf damage

Rice seedling test

Young rice seedlings ("Bahia" variety) were cultivated in nutrient solutions containing different concentrations of the active ingredients. After 6 days at 25° C. in continuous light, the active ingredient concentration was determined which reduced lengthwise growth of the second leaf-sheath by 50% (=KI$_{50}$).

(For details, see W. Rademacher and J. Jung, Berichte aus dem Fachgebiet Herbologie, Journal 24, pp. 127-134, University of Hohenheim, 1983).

The results are summarized in Table 14.

TABLE 14

| Compound No. | KI$_{50}$ (molar) |
|---|---|
| A | $1.5 \times 10^{-2}$ |
| D | $1.8 \times 10^{-4}$ |
| 2 | $1.4 \times 10^{-6}$ |
| 3 | $3.6 \times 10^{-6}$ |
| 6 | $1.6 \times 10^{-6}$ |
| 7 | $1.6 \times 10^{-6}$ |
| 13 | $6.0 \times 10^{-6}$ |
| 27 | $2.3 \times 10^{-6}$ |
| 30 | $2.9 \times 10^{-6}$ |
| 31 | $2.5 \times 10^{-6}$ |

TABLE 14-continued

| Compound No. | KI$_{50}$ (molar) |
| --- | --- |
| 32 | $2.9 \times 10^{-6}$ |
| 33 | $3.0 \times 10^{-6}$ |
| 34 | $3.5 \times 10^{-6}$ |
| 36 | $2.3 \times 10^{-6}$ |
| 38 | $2.1 \times 10^{-6}$ |
| 39 | $1.9 \times 10^{-6}$ |
| 76 | $2.7 \times 10^{-5}$ |
| 84 | $4.1 \times 10^{-5}$ |
| 85 | $2.0 \times 10^{-5}$ |
| 86 | $2.0 \times 10^{-5}$ |

We claim:

1. A cyclohexenone compound of the formula I

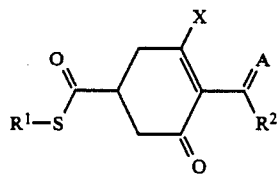 (I)

where $R^1$ is hydrogen; $C_1$-$C_6$-alkyl which is unsubstitued or substituted by $C_1$-$C_4$-alkoxy, $C_1$-$C_4$-alkylthio, $C_1$-$C_4$-dialkylamino, hydroxyl or halogen; $C_1$-$C_6$-alkenyl; $C_3$-$C_6$-cycloalkyl; or phenyl or benzyl which is unsubstituted or substituted by halogen, $C_1$-$C_4$-alkyl, $C_1$-$C_4$-alkoxy or nitro, $R^2$ is $C_1$-$C_4$-alkyl or cyclopropyl, A is oxygen; a radical $NOR^3$, where $R^3$ is $C_1$-$C_4$-alkyl, $C_3$- or $C_4$-alkenyl, $C_3$- or $C_4$-alkynyl, $C_2$-$C_4$-haloalkyl, $C_3$- or $C_4$-haloalkenyl or $C_2$-$C_4$-alkoxyalkyl; or a radical $NR^4$, where $R^4$ is hydrogen, $C_1$-$C_6$-alkyl, $C_1$-$C_4$-hydroxyalkyl, $C_1$-$C_4$-alkoxyalkyl, benzyl or phenyl, and X is hydroxyl; chlorine; $C_1$-$C_6$-alkylthio which is unsubstituted or substituted by $C_1$-$C_4$-alkoxy, $C_1$-$C_4$-alkylthio, $C_1$-$C_4$-dialkylamino, hydroxyl or halogen; $C_1$-$C_6$-alkenylthio; $C_3$-$C_6$-cycloalkylthio; or phenylthio or benzylthio which is unsubstituted or substituted by halogen, $C_1$-$C_4$-alkoxy or nitro.

2. A plant growth regulator containing inert additives and an effective amount of a cyclohexenone compound of the formula I as claimed in claim 1, where A is oxygen or a radical $NR^4$.

3. A method for regulating plant growth, wherein an effective amount of a cyclohexenone compound of the formula I as claimed in claim 1, where A is oxygen or a radical $NR^4$, is allowed to act on plants and/or their habitat.

4. A herbicide containing inert additives and an effective amount of a cyclohexenone compound of the formula I as claimed in claim 1, wherein A is a radical $NOR^3$.

5. A method of controlling undesirable plants, wherein the plants and/or the area to be kept free of the plants are treated with a herbicidally effective amount of a cyclohexenone compound of the formula I as claimed in claim 1, where A is a radical $NOR^3$.

* * * * *